United States Patent [19]

Weissbach

[11] Patent Number: 5,545,717
[45] Date of Patent: Aug. 13, 1996

[54] PLASMILAR AND PLASMILAR ANTIBODY COMPOSITIONS AS MALIGNANT CELL MARKERS

[75] Inventor: Lawrence Weissbach, Boston, Mass.

[73] Assignee: The General Hospital Corporation, Boston, Mass.

[21] Appl. No.: 242,035

[22] Filed: May 12, 1994

Related U.S. Application Data

[63] Continuation of Ser. No. 872,645, Apr. 21, 1992, abandoned.

[51] Int. Cl.$^6$ .............................. C07K 14/00; C12Q 1/68
[52] U.S. Cl. ............................ 530/324; 424/277.1; 435/6
[58] Field of Search ........................ 424/277.1; 530/350, 530/324; 435/6

[56] References Cited

PUBLICATIONS

Ichinose, Biochemistry 31, 3113 (1992)., "Multiple Members of the Plasminogen–Apolipoprotein(a) Gene Family Associated with Thrombosis.".
Forsgren et al. FEBS Lett. 213:254–260 (1987)., "Molecular cloning and characterization of a full–length cDNA clone for human plasminogen".
Horlow et al. "Antibodies: A laboratory manuel, Cold Spring Harbor Laboratories", (1988).
Robbins et al., "NH$_2$–Terminal Sequences of Mammalian Plasminogens and Plasmin S–Carboxymethyl Heavy (A) and Light (B) Chain Derivatives," J. Biol. Chem.; 248:7242–7246 (1973).
Hoylaerts et al., "Kinetics of the Activation of Plasminogen by Human Tissue Plasminogen Activator," J. Biol. Chem.; 257:2912–2919 (1982).
Saksela, "Plasminogen activation and regulation of pericellular proteolysis," Biochem. Biophys. Acta., 823: 35–65 (1985).
Holvoet et al., "A Monoclonal Antibody Specific for Lys-–plasminogen," J. Biol. Chem.; 260:12106–12111 (1985).
McLean et al., "cDNA sequence of human apolipoprotein(a) is homologous to plasminogen," Nature; 330:132–137 (1987).
Treadwell et al., "Cartilage Synthesizes the Serine Protease Inhibitor PAI-1: Support for the Involvement of Serine Proteases in Cartilage Remodeling," J. Ortho. Research; 9:309–316 (1991).
Petersen et al., "Characterization of the Gene for Human Plasminogen, a Key Proenzyme in the Fibrinolytic System," J. of Biological Chemistry 265:6104–6111, (1990).

Patthy et al., "Kringles:modules specialized for protein binding," FEBS Letters; 171:131–136 (1984).
Nakamura et al., "Molecular cloning and expression of human hepatocyte growth factor," Nature; 342:440–443 (1989).
Moscatelli et al., "Membrane and matrix localization of proteinases: a common theme in tumor cell invasion and angiogenesis," Biochimica et Biophysica Acta.; 948:67–85 (1988).
Collen et al., "Basic and Clinical Aspects of Fibrinolysis and Thrombolysis," Blood; 78:3114–3124 (1991).
Eeckhout et al., "Further Studies on the Activation of Procollagenase, the Latent Precursor of Bone Collagenase," J. Biochem; 166:21–31 (1977).
Liotta et al., "Cancer Metastasis and Angiogenesis: An Imbalance of Positive and Negative Regulation," Cell; 64:327–336 (1991).
Werb et al., "Endogenous Activation of Latent Collagenase by Rheumatiod Syynovial Cells," New England Journ. of Medicine; 296:1017–1023 (1977).
Miyazawa et al., "Molecular Cloning and Sequence Analysis of cDNA for Human Hepatocyte Growth Factor," Biochem. and Biophys. Research Comm.; 163:967–973 (1989).
Matrisian, "Metalloproteinases and their inhibitors in matrix remodeling," Reviews; 6:121–125 (1990).
Cruwys et al., "Cooperation between interleukin–1 and the fibrinolytic system in the degradation of collagen by articular chondrocytes," J. Pharmacol; 100:631–635 (1990).
Wiman et al., "Amino–Acid Sequence of the Cyanogen-–Bromide Fragment from Human Plasminogen that Forms the Linkage between the Plasmin Chains," J. Biochem.; 58:539–547 (1975).
Wiman, "Primary Structure of the B–Chain of Human Plasmin," Eur. J. Biochem.; 76:129–137 (1977).
Wiman et al., "Structural Relationship between 'Glutamic Acid' and 'Lysine' Forms of Human Plasminogen and Their Interaction With the NH$_2$–Terminal Activation Peptide . . . ," Eur. J. Biochem.; 50:489–494 (1975).
Tryggvason et al., "Proteolytic degradation of extracellular matrix in tumor invasion," Biochem. Biophys. Acta. 907:191–217 (1987).

Primary Examiner—Christine M. Nucker
Assistant Examiner—Lawrence J. Carroll, II
Attorney, Agent, or Firm—Fish & Richardson

[57] ABSTRACT

Disclosed are substantially pure plasmilar polypeptide and antibodies which bind plasmilar.

1 Claim, 3 Drawing Sheets

FIG. 1

```
              6    Y   V   N   T   Q   G   P   S   L   F   S   V   T
EXON         TAT  GTG AAT ACC CAG GGG CCT TCA CTG TTC AGT GTC ACT
                                          G                 30
              K   K   Q   L   G   A   G   S   R   E   E   C   A
             AAG AAG CAG CTG GGG GCA GGA AGC AGA GAA GAA TGT GCA
                                  A          T        40
              A   K   C   E   D   K   S   E   F   T   C   R
             GCA AAA TGT GAA GAG GAC AAA TTC GAA TTC ACC TGC AG
                              G          G       ===========

INTRON       gta ttt tca tcg ttg cac cta ccc aga aat ctg taa
                         c                   g
             ttc aga . . . . . . . approx. 1100 bp . . . . . .
                                     g
             tt  att aat aaa cat ttg ttt tct tta aat aaa gaa aaa
             tac tta ttg gat ttc ctg ctt cgt tct gca g
                                                  50
              A   F   Q   Y   H   S   K   E   Q   Q   C   V
EXON         G GCA TTC CAA TAT CAC AGT AAA GAG CAA CAG TGT GTG
                                     60                A
              I   M   A   E   N
             ATA ATG GCT GAA AAC A
```

PLASMILAR AND PLASMILAR ANTIBODY COMPOSITIONS AS MALIGNANT CELL MARKERS

This invention was made with Government support under Contract #AM 16265-17 awarded by the National Institutes of Health. The Government has certain rights in the invention.

This is a continuation of application Ser. No. 07/872,645, filed Apr. 21, 1992, now abandoned.

BACKGROUND OF THE INVENTION

The invention relates to diagnostic markers for malignant cells.

Plasminogen, a serine proteinase precursor secreted by the liver, plays a pivotal role in dissolving blood clots (Saksela, *Biochim. Biophys. Acta* 823:35, 1985; Collen and Lijnen, *Blood* 78:3114, 1991). Cleavage of a specific Arg-Val peptide bond by either tissue-type or urokinase-type plasminogen activator along with autocatalytic removal of an N-terminal preactivation peptide produces the active two-chain proteinase plasmin. Plasmin is capable of attacking fibrin, a principal component of clots, thereby facilitating clot lysis (Robbins et al, *J. Biol. Chem.* 248:7242, 1973; Hoylaerts et al., *J. Biol. Chem.* 257:2912, 1982; Holvoet et al., *J. Biol. Chem.* 260:12106, 1985). In addition to its well-characterized thrombolytic capability, plasmin has been implicated along with other proteinases as a mediator of tissue remodeling during development (Matrisian, *Trends Genet.* 6:121, 1990), cartilage destruction in osteoarthritis (Eeckhout and Vaes, *Biochem. J.* 166:21, 1977; Werb et al., *N. Engl. J. Med.* 269:1017, 1977; Cruwys et al., *J. Pharmacol.* 100:631, 1990; Treadwell et al., *J. Orth. Res.* 9:309, 1991), and basement membrane invasion by metastatic tumor cells (Saksela, 1985, Supra; Tryggvason et al., *Biophys. Acta* 907:191, 1987; Moscatelli and Rifkin, *Biochem. Biophys. Acta* 948:67, 1988; Liotta et al., *Cell* 64:327, 1991).

Plasminogen is composed of an N-terminal preactivation peptide, a central section containing five adjacent homologous domains called kringles (Patthy et al., *FEBS Lett.* 171:131, 1984), and a C-terminal catalytic region (Wiman and Wallen, *Eur. J. Biochem.* 50:489, 1975; Wiman and Wallen, *Eur. J. Biochem.* 58:539, 1975; Wiman, *Eur. J. Biochem.* 76:129, 1977; Sottrup-Jensenet al., *Prog. Chem. Fibrinol. Thrombol.* 3:191, 1978).

A single gene for plasminogen has been reported from which the liver mRNA is derived (Forsgren et al., *FEBS Lett.* 213:254, 1987; Peterson et al., *J. Biol. Chem.* 265:6104, 1990). Recent duplications of at least portions of the plasminogen gene have occurred. For example, the apolipoprotein (a) gene contains extremely homologous domains, with similarity at the nucleotide level of greater than 90% in some areas (McLean et al., *Nature* 330:132, 1987). The plasminogen gene family also includes several coagulation proteins as well as hepatocyte growth factor (Miyazawa et al., *Biochem. Biophys. Res. Commun.* 163:967, 1989, Nakamura et al., *Nature* 342:440–443, 1989).

SUMMARY OF THE INVENTION

In general, the invention features a method of detecting a malignant cell (preferably, a metastatic malignant cell, a breast cancer cell, a hepatoma cell, or an osteosarcoma cell) in a biological sample. The method involves measuring plasmilar gene expression in the sample, an increase in plasmilar expression (relative to an equivalent wild-type sample) being indicative of the presence of the malignant cell. Because most cells types do not express detectable levels of plasmilar product, this assay generally involves a qualitative determination of whether plasmilar can be newly detected in the sample. A more careful comparison with a wild-type control is however recommended when diagnosing a sample from a tissue (such as liver or chondrocytes) which normally expresses the plasmilar gene.

The presence of a malignant cell in the sample is further indicated by a decrease in plasminogen expression in the plasmilar-expressing sample. Again, this decrease in plasminogen expression is determined by comparison with a wild-type control sample.

In preferred embodiments, plasmilar expression is measured by (a) isolating RNA from the biological sample; (b) synthesizing cDNA from the RNA; and (c) measuring plasmilar cDNA, an increase in the quantity of plasmilar cDNA (relative to a wild-type control) being indicative of the presence of the malignant cell. The method may also involve PCR amplification of the cDNA prior to measuring. Plasmilar expression is preferably determined by screening for nucleic acid having a nucleic acid sequence substantially identical to the nucleic acid sequence: TAT GTG AAT ACC CAG GGG CCT TCA CTG TTC AGT GTC ACT AAG AAG CAG CTG GGG GCA GGA AGC AGA GAA GAA TGT GCA GCA AAA TGT GAA GAG GAC AAA GAA TTC ACC TGC AG (SEQ ID NO: 1); or the nucleic acid sequence: G GCA TTC CAA TAT CAC AGT AAA GAG CAA CAG TGT GTG ATA ATG GCT GAA AAC A (SEQ ID NO: 2).

The invention also features substantially pure plasmilar DNA. Preferably, such DNA is cDNA; includes an exon sequence shown in FIG. 1 (SEQ ID NO:3) and is expressed at low levels (i.e., at levels significantly lower than plasminogen) in liver.

In related aspects, the invention features a vector and a cell which includes the substantially pure plasmilar DNA of the invention; and a method of producing a recombinant plasmilar polypeptide or a fragment or analog thereof which involves: (a) providing a cell transformed with DNA encoding plasmilar or a fragment or analog thereof positioned for expression in the cell; (b) culturing the transformed cell under conditions for expressing the DNA; and (c) isolating the recombinant plasmilar polypeptide.

The invention further features substantially pure plasmilar polypeptide. Preferably, the plasmilar polypeptide includes an amino acid sequence substantially identical to the amino acid sequence shown in FIG. 1 (SEQ ID NO:4); is expressed in metastatic breast cancer tissue, osteosarcomas, and hepatomas; and is expressed at low levels (i.e., at levels significantly lower than plasminogen) in liver.

Finally, the invention features a substantially pure antibody which specifically binds to a plasmilar polypeptide; and a therapeutic composition which includes such an antibody formulated in a physiologically-acceptable carrier. This therapeutic composition may be administered to a mammal in a dosage effective to reduce metastasis of malignant cells as a treatment for cancer.

By "substantially pure polypeptide" is meant that the plasmilar polypeptide provided by the invention is at least 60%, by weight, free from the proteins and naturally-occurring organic molecules with which it is naturally associated. Preferably, the preparation is at least 75%, more preferably at least 90%, and most preferably at least 99%, by weight, plasmilar polypeptide. A substantially pure plasmilar polypeptide may be obtained, for example, by extraction from a natural source (e.g., a mammalian chondrocyte cell or metastatic cell); by expression of a recombinant nucleic acid encoding a plasmilar polypeptide, or by chemically synthesizing the protein. Purity can be measured by any appropriate method, e.g., column chromatography, polyacrylamide gel electrophoresis, or HPLC analysis. By a "polypeptide" is meant any chain of amino acids, regardless of length or post-translational modification (e.g., glycosylation).

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein or domain (assayed, e.g., as described herein). A "substantially identical" nucleic acid sequence codes for a substantially identical amino acid sequence as defined above.

By "substantially pure DNA" is meant DNA that is free of the genes which, in the naturally-occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "transformed cell" is meant a cell into which (or into an ancestor of which) has been introduced, by means of recombinant DNA techniques, a DNA molecule encoding (as used herein) a plasmilar polypeptide.

By "positioned for expression" is meant that the DNA molecule is positioned adjacent to a DNA sequence which directs transcription and translation of the sequence (i.e., facilitates the production of, e.g., plasmilar polypeptide).

By "substantially pure antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight plasmilar-specific antibody. A substantially pure plasmilar-specific antibody may be obtained, for example, by affinity chromatography using recombinantly-produced plasmilar polypeptide and standard techniques.

By "specifically binds", as used herein, is meant an antibody which recognizes and binds a plasmilar polypeptide but which does not substantially recognize and bind other molecules in a sample, e.g., a biological sample, which naturally includes plasmilar polypeptide.

Applicant's have identified a novel gene, termed plasmilar, whose increased expression correlates with the presence of malignant cells (particularly, metastatic malignant cells). Accordingly, plasmilar expression provides a diagnostic tool for early cancer detection or for the monitoring of cancer regression during therapy. Applicants have further provided a preferred RNA-PCR based assay for detection of plasmilar expression (and therefore of malignant cells) which is very rapid and unusually sensitive

DETAILED DESCRIPTION

The drawings will first briefly be described.
Drawings

There now follows a description of the isolation and characterization of a human plasmilar cDNA as well as a description of a preferred means of detecting plasmilar expression in a biological sample. This example is provided for the purpose of illustrating the invention and should not be construed as limiting.

IDENTIFICATION OF THE PLASMILAR GENE

Plasmilar was discovered during applicant's investigation of plasminogen gene expression in non-hepatic tissue (specifically, in chondrocyte tissue). RNA-PCR was employed as a particularly sensitive assay for gene expression, with a region targeted for cDNA amplification extending from three amino acids upstream of the plasminogen signal peptide cleavage site to plasminogen amino acid 68. This region of cDNA encodes a significant portion of the "preactiviation peptide," a peptide which is autolytically cleaved by plasmin between $Lys_{77}$ and $Lys_{78}$ to produce a truncated plasminogen polypeptide (Wallen and Wiman, supra; Robbins et al., supra), termed Lys-plasminogen, a superior substrate for tPA compared to the full length (i.e., Gluplasminogen) species (Hoylaerts et al., supra). This area of the plaminogen gene contains a single intron located within the codon for $Arg_{43}$ and a single EcoRI restriction site located within the coding region (Petersen et al., supra). Because this preactivation peptide domain is not present in the otherwise homologous apolipoprotein (a) gene, undesired amplification of this gene is avoided (McLean et al., supra).

RNA-PCR was carried out as follows. Total RNA, isolated from chondrocytes by the guanidinium-thiocyanatephenol procedure of Chomczyniski and Sacchi (*Anal. Biochem.* 162:156, 1987) was used as template for reverse transcriptase (Sambrook et al., *Molecular Cloning: A Laboratory Manual*, 2nd Ed., Cold Spring Harbor Laboratory, Cold Spring Harbor, N.Y., 1989). The reverse transcriptase reaction mixture (in a total volume of 10 μl) contained 1.0 mM of each dNTP, 50 mM Tris-HCl, pH 8.0, 75 mM KCl, 3 mM $MgCl_2$, 10 mM DDT, 1–2 μg of total RNA, 20 pM of the plasminogen gene-specific antisense primer (SEQ ID NO:6; see below) and 200 units of Superscript Reverse Transcriptase (Gibco/BRL, Gaithersburg, Md.). Prior to adding the enzyme and DTT, the reaction mixture was incubated at 70° C. for 10 min and quick chilled on ice. The DTT was then added, and the reaction mixture was warmed to 42° C. for 2 min. Finally, the reverse transcriptase was added, and the incubation was continued at 42° C. for 60 min.

One-half of the cDNA products was used in the subsequent polymerase chain reaction (PCR). Amplification of the desired region of cDNA was accomplished by adding (in a total volume of 100 ul) 5 μl of the final cDNA reaction mixture (above), 10 mM Tris HCl, pH 8.8, 50 mM KCl, 200 μM of each dNTP, 1.5 mM $MgCl_2$, 0.1% Triton X-100, 100 pm of the appropriate primers (synthesized by Oligos etc., Guifford, Conn.; described below) and 2–4 units of Taq thermostable DNA polymerase (Promega, Madison, Wis.). To prevent nonspecific annealing of primer to the cDNA, the reaction samples lacking the Taq DNA polymerase were heated (i e., "hot start") to 85° C. in a heating block for 2 minutes prior to addition of the DNA polymerase, and the tubes immediately placed in a Biocycler air-driven thermal cycler (Bios, Inc., New Haven, Conn.) already pre-warmed to 94° C. for 60 sec. Annealing of the primers was carried out at 60° C. for 60 sec, and elongation by the DNA polymerase was allowed to proceed at 72° for 60 sec. A total of 30 cycles was performed. The primers used for the PCR reaction were of sequence:

5' GGTCAAGGAGAGCCTCTGGATGAC 3' (SEQ ID NO: 5; sense primer) beginning nine nucleotides upstream of the plasminogen signal peptide cleavage site and 5' CCTAATGATTATGGAGGACTTCC 3' (SEQ ID NO: 6; antisense primer) encompassing plasminogen amino acids 61–68. To insure that cDNA or pseudogene contamination (within the genomic DNA) was not responsible for the final PCR products, parallel reactions were routinely performed lacking reverse transcriptase to demonstrate product dependence on the enzyme activity. To enable digestion by restriction enzymes, the PCR products were passed over Chroma Spin-100 columns (Clontech; Palo Alto, Calif.), and concentrated by ethanol precipitation. After digestion with the appropriate restriction enzyme, the products were electrophoresed in 1.5% agarose gels, stained with ethidium bromide, and photographed.

Amplifications of cDNA corresponding to chondrocyte RNA produced the expected size product of 213 bp, which contained a single EcoRI restriction site as predicted for the plasminogen gene. Using methods identical to those described above, cDNA corresponding to metastatic breast tissue RNA also produced a 213 bp product with the predicted EcoRI site.

To confirm their identity, the chondrocyte PCR products were subcloned. Specifically, the products were made blunt-ended with DNA polymerase I, and phosphorylated with polynucleotide kinase. The resultant species were then inserted into SmaI-cut, dephosphorylated pGEM-3Z (Promega; Madison, Wis.). Ligated products were transformed into DH5α transformation-competent bacterial cells (GIBCO/BRL; Grand Island, N.Y.), and three independent insert-containing plasmids were sequenced by the dideoxy chain termination method of Sanger et al. (*Proc. Natl. Acad. Sci. USA* 74:5463, 1977) using Sequenase (Tabor and Richardson, *Proc. Natl. Acad. Sci. USA* 84:4767, 1987) obtained from Promega.

Two similar but distinct sequences were obtained. One species matched precisely with the previously reported liver plasminogen cDNA sequence. The homologous but distinct cDNA fragment (represented by two different clones) contained seven nucleotide changes. This fragment matched a subcloned cDNA species from the metastatic breast cancer PCR products (obtained as described above for the chondrocyte products).

Figure 1:
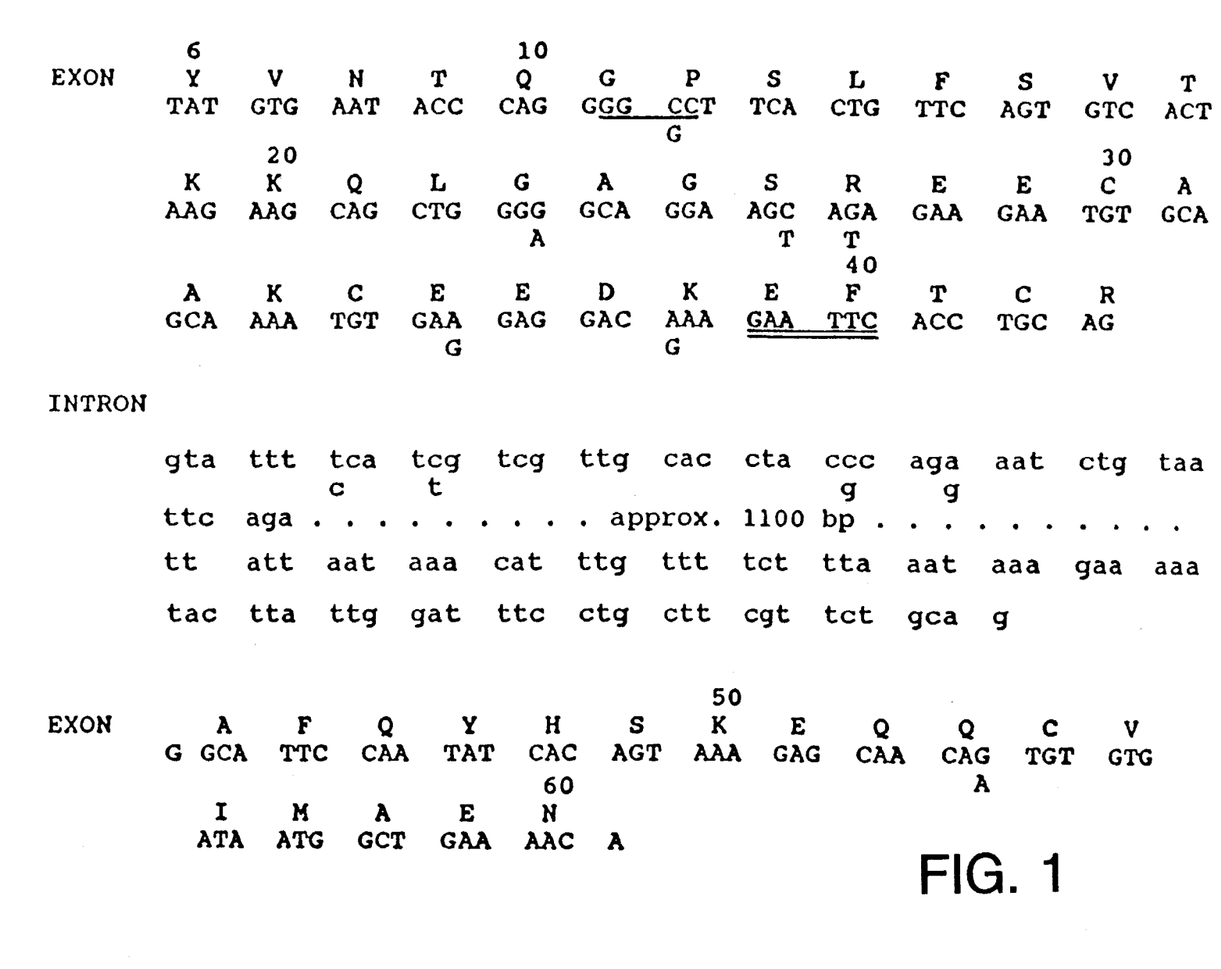
FIG. 1 shows the nucleotide sequence (SEQ ID NO:3) and the deduced amino acid sequence (SEQ ID NO:4) of a plasmilar partial-length cDNA and intron sequence.

This novel cDNA fragment, termed plasmilar, is shown in FIG. 1. The coding strand within the region demarcated by the PCR primers is presented in capital letters; the numbering of the amino acids is based on an alignment with the published plasminogen cDNA sequence (Forsgren et al., supra; Petersen et al., supra), with number 6 representing the sixth amino acid after the signal peptide cleavage site. The nucleotides shown below the plasmilar DNA sequence denote the corresponding bases which differ in the plasminogen gene. Three of the seven base changes result in amino acid substitutions, specifically: $Pro_{12}$, $Arg_{27}$, and $Lys_{38}$ (as numbered in FIG. 1). The nucleotide sequences from which the primers in the PCR were designed occur immediately before and after the displayed exon sequences. The EcoRI restriction site common to both the plasmilar and plasminogen cDNAs is denoted by a double underline. Additional plasmilar sequence (termed PRG B) is provided in Ichinose, *Biochemistry* 31:3113, 1992, and the entire coding sequence can be seen in SEQ ID NO: 11.

Figure 2:
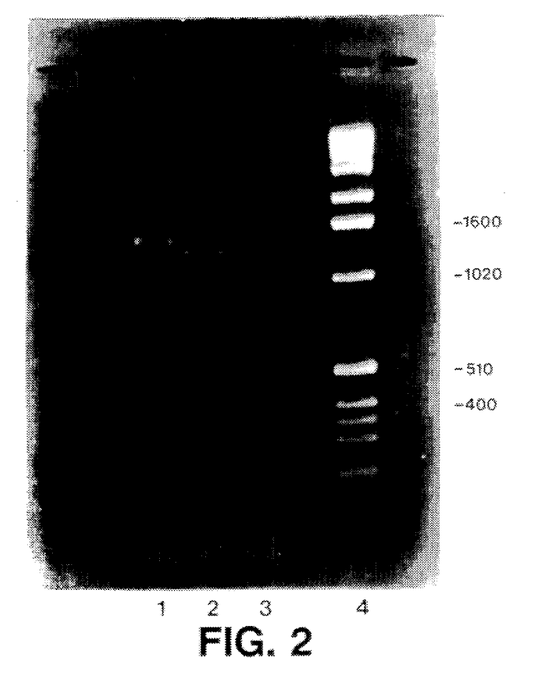
FIG. 2 shows a restriction analysis of genomic plasmilar and plasminogen genes.

To further distinguish plasmilar from plasminogen, restriction enzyme analysis of genomic DNA was carried out. Specifically, human placental genomic DNA (Clontech, Palo Alto, Calif.) was PCR amplified using the primers and methods described above, except that cDNA synthesis was not required and the denaturation and elongation steps in the thermocycling were increased to 120 sec. The PCR products were electrophoresed in a 1.5% agarose gel, and a single product band of approximately 1400 bp was observed (FIG. 2, lane 1). Digestion with EcoRI yielded two fragments, consistent with a single cleavage within the coding region of the amplified product (FIG. 2, lane 2).

Toward providing an assay to distinguish plasmilar, applicants capitalized on one of the observed nucleotide differences between the plasmilar and plasminogen sequences (FIG. 1). The residue at nucleotide 19 in the plasmilar gene fragment (or nucleotide 43 from the 5' end if the sense primer is counted) creates a HaeIII restriction site unique to plasmilar; in FIG. 1, this is shown as a single underline in the plasmilar sequence. There are no other HaeIII restriction sites in the amplified cDNA region of either plasminogen or plasmilar (FIG. 1). In addition, the PRG A gene reported by Ichinose (supra) is like plasminogen in that it does not contain a HaeIII site in this region.

Accordingly, if both genes are represented in a sample, digestion of the 1400 bp genomic PCR product with HaeIII should yield two DNA fragments separated by 43 bp (with the possibility of additional DNA fragments being produced if HaeIII restriction sites are present in the introns), and the sum of the individual HaeIII fragments should total more than 1400 bp, due to the differential cleavage of the two sequences by HaeIII. As shown in lane 3 of FIG. 2, both plasminogen and plasmilar are present in the human genomic PCR products. A doublet differing in length by approximately 50 bp is evident (specifically, containing bands of 700 and 750 base pairs), and the sum of the fragments is 2000 base pairs, significantly greater than the predicted 1400 base pairs. The DNA fragments comprising the doublet are present in equivalent amounts, demonstrating that the primer pair recognizes each gene with approximately equal affinity. This allows a semi-quantitative measurement of plasmilar steady-state RNA levels relative to plasminogen RNA levels in the RNA-PCR experiments (see below).

Sequencing of seven amplified genomic DNA isolates (i.e., containing subcloned 1400 bp PCR products) revealed four sequences matching plasminogen and three sequences identical to plasmilar. The partial intron sequence for plasmilar is shown in FIG. 1; sequence homology with plasminogen (equivalent in degree to that found in the exon regions) persisted in the untranslated region.

Plasmilar Expression

Several tissues and cell lines were tested for their synthesis of both plasminogen and plasmilar RNA, using sensitivity of the RNA-PCR products to HaeIII cleavage as a diagnostic test. Based on the results presented in FIG. 2, it appears that the percentage of Hae III-cleaved PCR product gives a fairly accurate estimation of plasmilar mRNA levels relative to plasminogen mRNA amounts.

Expression of plasmilar and plasminogen was first assayed in metastatic breast cancer tissue, normal breast tissue, and normal adult liver. The normal breast tissue was obtained from a biopsy sample and was determined to be free of cancer cells by histological examination. The breast cancer tissue was a stage III metastatic carcinoma which was isolated from the right proximal femur of a 57 year old female. As a positive marker for the breast carcinoma, the presence of stromelysin-3 (distinct from matrix metalloproteinase-3) RNA was assayed. The stromelysin-3 gene is expressed by stromal cells immediately surrounding malignant (but not benign) breast cancer cells and is not transcribed in many normal tissues (Basset et al., *Nature* 348:699, 1990). The primer pair used to amplify the cDNA was:

5' CTTCGGTTCCCATGGCAGTTGGTG 3' (SEQ ID NO: 7; sense primer, nt 352–375) and

5' GGAAGAACCAAATGTGGCCCTGGGCATCC 3' (SEQ ID NO: 8; antisense primer, nt. 1054–1081).

The PCR products were analyzed by Southern procedure (Sambrook et al., *Molecular Cloning: A Laboratory Manual*, 2nd ED., Cold Spring Harbor Laboratory, Cold Spring Harbor, N.Y., 1989) with a stromelysin-3 cDNA probe. As a control for the integrity of the RNA preparations, RNA-PCR was performed using a primer pair which bracketed a region of the human 18S rRNA (Torczynski et al., *DNA* 4:2831985):

5' TAACGAACGAGACTCTGGCATGC 3' (SEQ ID NO: 9; sense primer, nt 1478-1500) and

5' AGCTTATGACCCGCACTTACTGG 3' (SEQ ID NO: 10; antisense primer, nt 1746-1768).

Comparable amounts of rRNA were present in the normal breast tissue and cancerous breast tissue (as well as in the cultured chondrocyte RNA preparation utilized below).

Figure 3:
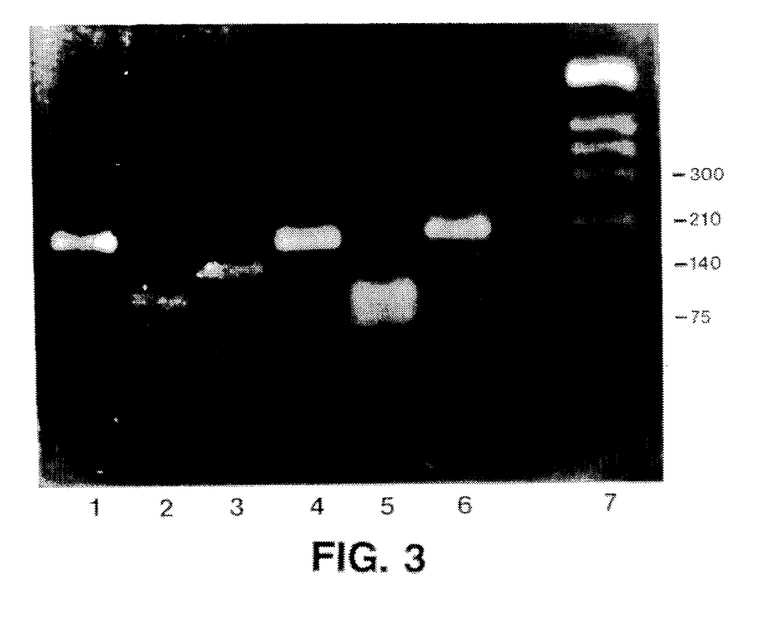
FIG. 3 shows a restriction analysis of PCR products generated from metastatic breast cancer tissue RNA (lanes 1–3) and normal adult liver RNA (lanes 46).

FIG. 3 shows the restriction analysis results for the RNA-PCR products generated from metastatic breast cancer tissue RNA and adult liver RNA. In lanes 1–3, RNA from the breast cancer tissue was used as template, while in lanes 4–6 RNA from liver was employed as template. Lanes 1 and 4 represent the uncut products; lanes 2 and 5 demonstrate the effect of EcoRI cleavage; and lanes 3 and 6 test the sensitivity of the PCR products to HaeIII cleavage. The numbers to the right denote the length in bp of standard DNA markers.

Comparison of the uncut products derived from the breast cancer RNA shown in lane 1 to the same products following HaeIII digestion in lane 3 demonstrates that the products are completely sensitive to HaeIII attack, thus signifying that only the plasmilar gene is expressed in breast cancer tissue. In contrast, normal breast tissue did not transcribe detectable amounts of either plasmilar or plasminogen mRNA (data not shown). The liver, a documented source of plasminogen mRNA, transcribed predominately the plasminogen gene; HaeIII cleaved less than 20% of the liver PCR products (FIG. 3, lane 6).

In another example, plasmilar expression in normal chondrocytes was compared with plasmilar expression in an osteosarcoma cell line. Normal human articular cartilage was obtained from the knee joint of a 14 year old male patient who underwent surgery for a leg amputation as a result of an osteosarcoma. The osteosarcoma did not involve the knee joint. Chondrocytes were separated from the extracellular matrix by collagenase treatment, and cultured in Dulbecco's Eagle medium supplemented with 10% fetal calf serum. These cultured chondrocytes contained no detectable stromelysin-3 mRNA as measured. The MG-63 cell line (ATCC Accession No. CRL 1427; American Type Culture Collection, Rockville, Md.) was the source of the osteosarcoma cells.

Figure 4:
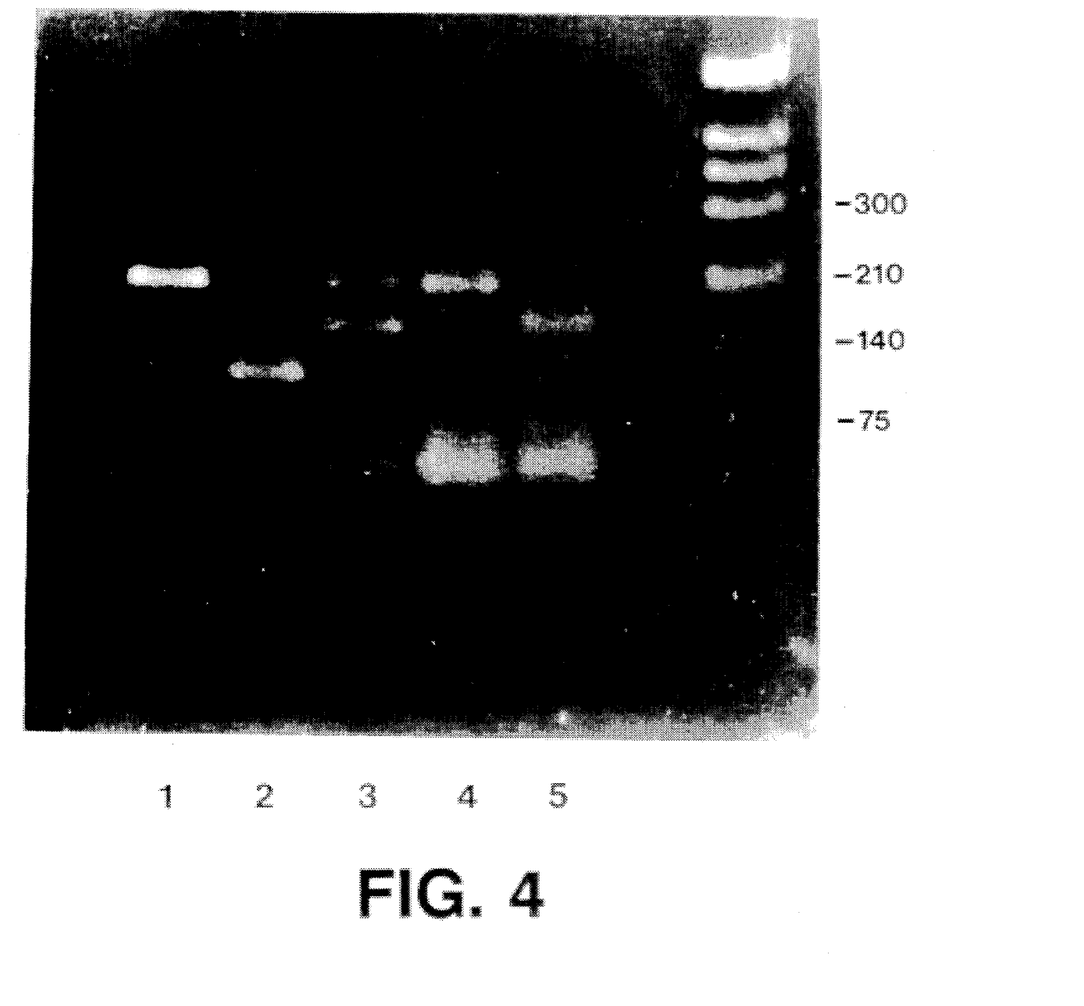
FIG. 4 shows a restriction analysis of PCR products generated from normal chondrocyte RNA (lanes 1–3) and from osteosarcoma cell line MG-63 RNA (lanes 4 and 5).

FIG. 4 shows the restriction analysis results from the RNA-PCR products generated from normal chondrocyte RNA or the osteosarcoma cell line MG-63. Lanes 1–3 depict the chondrocyte RNA-PCR products; lanes 4 and 5 depict the MG- 63 RNA-PCR products. Lanes 1 and 4 show undigested products, lane 2 shows products cleaved with EcoRI, and lanes 3 and 5 show products after treatment with HaeIII. The numbers to the right refer to the length in bp of standard DNA markers.

The results shown in FIG. 4 demonstrate that cultured normal chondrocytes expressed approximately equal amounts of plasmilar and plasminogen transcripts (lane 3), while the osteosarcoma cell line expressed only plasmilar transcripts (lane 5). The transcription of both genes in normal chondrocytes may be pertinent to the connective tissue destructive capability of these proteins, evident during tissue remodeling as well as certain pathological states such as osteoarthritis.

These data suggest a pattern of expression of the two genes, whereby plasminogen is expressed solely in normal cells (e.g. hepatocytes and chondrocytes) and plasmilar is synthesized in both normal and cancerous cells. To further test this hypothesis, total RNA was prepared from a metastatic osteosarcoma and a liver hepatoma cell line Hep3B. The metastatic osteosarcoma tissue was removed from the lung of a 73 year old female and was determined to be osteosarcoma-derived by histological examination. Hep3B is available from the American Type Culture Collection (ATCC Accession No. HB8064). RNA-PCR revealed that both the metastatic osteosarcoma-derived PCR products and the hepatoma-derived PCR products were completely sensitive to HaeIII cleavage, consistent with the fact that both are malignant cells.

The function of plasmilar is unknown. However, it may, like plasmin, be a proteinase. If the plasmilar-encoded polypeptide does indeed possess proteinase activity, it is possible that plasmilar enzymatic activity is essential for malignant cancer cells to infiltrate basement membranes of foreign tissues and ultimately lodge within the interstitial stroma. This process of tumor metastasis, which is a primary cause of mortality for cancer patients, most likely requires an array of extracellular matrix degradative enzymes including proteinases (such as plasmin and metalloproteinases) and glycosidases (such as heparinase) (Moscatelli and Rifkin, supra; Liotta et al., supra). In addition to directly cleaving extracellular framework proteins, plasmin is thought to be the in vivo activator of latent metalloproteinases (Paranjpe et al., *Life Sci*. 26:1223, 1980; Salo et al., *Int. J. Cancer* 30:669, 1982; He et al., *Proc. Natl. Acad. Sci. USA* 86:2632, 1989); plasmilar may similarly cooperate with other degradative enzymes to facilitate destruction of extracellular matrix proteins, e.g., those comprising the basement membrane.

Cloning the Plasmilar cDNA

Identification of the plasmilar fragments described above facilitates the cloning of the full-length plasmilar cDNA as follows. A cDNA library is constructed (e.g., in a bacteriophage vector) by standard techniques from poly (A)-enriched RNA isolated from any appropriate plasmilar-expressing cell type (e.g., osteosarcoma or breast cancer cells). This library is screened for plasmilar cDNA sequences by standard hybridization screening techniques employing a PCR-derived plasmilar cDNA probe (e.g., a probe which includes one or preferably both of the exon sequences shown in FIG. 1). Such standard techniques for screening recombinant DNA libraries are described in Ausubel et al. (*Current Protocols in Molecular Biology*, John Wiley & Sons, New York, 1989).

Polypeptide Expression and Purification

In general, polypeptides according to the invention may be produced by transformation of a suitable host cell with all or part of a plasmilar-encoding cDNA fragment (e.g., the cDNAs described above) in a suitable expression vehicle.

Those skilled in the field of molecular biology will understand that any of a wide variety of expression systems may be used to provide the recombinant protein. The precise host cell used is not critical to the invention. Plasmilar polypeptide may be produced in a prokaryotic host (e.g., *E. coli*) or in a eukaryotic host (e.g., *Sacchoromyces cerevisiae* or mammalian cells, e.g., COS 1, NIH 3T3, or L cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1989). The method of transformation or transfection and the choice of expression vehicle will depend on the host system selected. Transformation and transfection methods are described, e.g., in Ausubel et al. (*Current Protocols in Molecular Biology*, John Wiley & Sons, New York, 1989); expression vehicles may be chosen from those provided, e.g., in *Cloning Vectors: A Laboratory Manual* (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding plasmilar or an appropriate fragment or analog (as described herein) would be inserted into the pMAMneo vector in an orientation designed to allow expression. The recombinant protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, plasmilar (or a fragment or analog) is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the receptor (or receptor fragment or analog) is cloned into an expression vector which includes the dihydrofolate reductase (DHFR) gene. Integration of the plasmid and, therefore, the plasmilar-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). Any of the host cells described above or, preferably, a DHFR-deficient CHO cell line (e.g., CHO DHFR cells, ATCC Accession No. CRL 9096) are among the host cells preferred for DHFR selection of a stably-transfected cell line or DHFR-mediated gene amplification.

Once the recombinant plasmilar protein (or fragment or analog, thereof) is expressed, it is isolated, e.g., using affinity chromatography. In one example, an anti-plasmilar antibody (e.g., produced as described herein) may be attached to a column and used to isolate intact plasmilar or plasmilar fragments or analogues. Lysis and fractionation of plasmilar-harboring cells prior to affinity chromatography may be performed by standard methods (see, e.g., Ausubel et al., supra). Alternatively, a plasmilar fusion protein, for example, a plasmilar-maltose binding protein, a plasmilar-β-galactosidose, or a plasmilar-trpE fusion protein, may be constructed and used for isolation of plasmilar protein (see, e.g., Ausubel et al., supra; New England Biolabs, Beverly, Ma.).

Once isolated, recombinant plasmilar protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Plasmilar polypeptides of the invention, particularly short fragments, can also be produced by chemical synthesis (e.g., by the methods described in *Solid Phase Peptide Synthesis*, 2nd ed., 1984 The Pierce Chemical Co., Rockford, Ill.).

Antibody Production

Using a plasmilar polypeptide described above (e.g., the recombinant protein or a chemically synthesized plasmilar peptide based on its deduced amino acid sequence), polyclonal antibodies which bind specifically to a plasmilar polypeptide may be produced by standard techniques (see, e.g., Ausubel et al., supra) and isolated, e.g., following peptide antigen affinity chromatography. Monoclonal antibodies can also be prepared using standard hybridoma technology (see, e.g., Kohler et al., *Nature* 256:495, 1975; Kohler et al., *Eur. J. Immunol.* 6:511, 1976; Kohler et al., *Eur. J. Immunol.* 6:292, 1976; Hammerling et al., in *Monoclonal Antibodies and T cell Hybridomas*, Elsevier, N.Y., 1981; and Ausubel et al., supra). Such a monoclonal antibody preferably binds plasmilar but not plasminogen (as determined by standard screening techniques).

In general, antibodies according to the invention preferably do not bind plasminogen. However, absolute specificity is not required, particularly for carrying out detection assays on tissues which do not express plasminogen protein. To date, plasminogen expression has been detected in the following human tissues: liver, eosinophils, kidney, and chondrocytes, and no others.

Plasmilar Detection Assays

Described above is a preferred RNA-PCR method for detecting plasmilar expression in a biological sample. Applicant has provided sample primers for PCR amplification of the plasmilar gene. However, any number of other suitable primers can also be utilized; general guidance for choosing primers and carrying out PCR methods can be found in Ausubel et al. (supra) and *PCR Technology: Principles and Applications for DNA Amplification* (ed., H. A. Ehrlich, Stockton Press, N.Y.).

A number of other assays are also suitable for identification of plasmilar expression (and therefore malignant cells) in a sample aliquot.

For example, other nucleic acid detection methods, although less preferable, may be used. These include hybridization screening of a cDNA library isolated from the biological sample (e.g., isolated as described above); such hybridization is carried out by standard techniques (see, e.g., Sambrook et al., *Molecular Cloning: A Laboratory Manual,* 2d ed., Cold Spring Harbor Press, NY; and Ausubel et al., supra) using hybridization probes based on FIG. 1 or other sequences of the full-length plasmilar cDNA which do not cross hybridize with plasminogen. The cDNA library may be, but does not need to be, PCR-amplified prior to hybridization.

Immunoassays may also be used to detect plasmilar protein in a biological sample. Plasmilar-specific polyclonal, or preferably monoclonal, antibodies may be used in any standard immunoassay format (e.g., ELISA, Western blot, or RIA assay), including competitive immunoassays, to detect a plasmilar polypeptide in a biological sample. Production of such antibodies is described above. Examples of such assays are described, e.g., in Ausubel et al., supra.

Immunohistochemistry techniques may also be utilized for plasmilar detection. A tissue sample is obtained from a patient, and a section stained for the presence of plasmilar using an anti-plasmilar antibody (prepared as described above) and any detection system (e.g., one including a secondary antibody conjugated to horseradish peroxidase). General guidance regarding such techniques can be found in, e.g., Bancroft and Stevens, *Theory and Practice of Histological Techniques,* Churchill Livingstone, 1982; and Ausubel et al., supra.

Finally, slide PCR may be used for plasmilar detection. According to this technique, the cell or tissue sample is mounted on a slide, and the PCR reaction (as described above) is carried out directly on the slide, facilitating automated plasmilar PCR detection. This technique is generally described by Yap and McGee, *Nucl. Acids. Res.* 19:4294, 1991.

Use

Identification of the plasmilar sequence facilitates the development of assays (e.g., those described herein) for the detection of malignant cells in a sample. Such assays include nucleic acid detection assays (which utilize the plasmilar nucleic acid molecules described herein) as well as immunoassays (which utilize the instantly-described plasmilar polypeptides and plasmilar-specific antibodies).

Because of plasmilar's involvement in malignant cell metastasis and because (based on its small size) plasmilar may represent a growth factor, administration of plasmilar-specific antibodies or other such plasmilar antagonists may provide an effective treatment for cancer. The antibody or antagonist is administered as a therapeutic preparation (e.g., in physiological saline) in accordance with the cancer to be treated. Ordinarily, it will be administered intravenously, at a dosage effective to reduce metastasis. Alternatively, it may, for some cancers, be more appropriate or convenient to administer the therapeutic orally, nasally, or topically, e.g., as a liquid or spray. Again, the dosages are as described above. Treatment may be repeated as necessary for alleviation of disease symptoms. Treatment may also be combined with other cancer therapies aimed at destroying malignant cells, e.g., chemotherapy or radiation therapy.

The diagnostic and therapeutic methods of the invention may be used for detection of malignant cells or treatment of any mammal, for example, humans, domestic pets, or livestock. Where a non-human mammal is diagnosed or treated, the plasmilar polypeptide, nucleic acid, or antibody is preferably specific for that species.

Other embodiments are within the claims.

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
( A ) LENGTH: 113
( B ) TYPE: nucleic acid
( C ) STRANDEDNESS: single
( D ) TOPOLOGY: linear ( x i ) SEQUENCE DESCRIPTION: SEQ ID NO: 1:

TATGTGAATA CCCAGGGGCC TTCACTGTTC AGTGTCACTA AGAAGCAGCT GGGGGCAGGA     60

AGCAGAGAAG AATGTGCAGC AAAATGTGAA GAGGACAAAG AATTCACCTG CAG           113

( 2 ) INFORMATION FOR SEQ ID NO: 2:

( i ) SEQUENCE CHARACTERISTICS:
( A ) LENGTH: 53
( B ) TYPE: nucleic acid
( C ) STRANDEDNESS: single
( D ) TOPOLOGY: linear ( x i ) SEQUENCE DESCRIPTION: SEQ ID NO: 2:

GGCATTCCAA TATCACAGTA AAGAGCAACA GTGTGTGATA ATGGCTGAAA ACA            53

(2) INFORMATION FOR SEQ ID NO: 3:

(i) SEQUENCE CHARACTERISTICS:
      (A) LENGTH: 280
      (B) TYPE: nucleic acid
      (C) STRANDEDNESS: single
      (D) TOPOLOGY: linear (xi) SEQUENCE DESCRIPTION: SEQ ID NO: 3:

| | | | | | | | | | | | | | | | | |
|---|---|---|---|---|---|---|---|---|---|---|---|---|---|---|---|---|
| TAT | GTG | AAT | ACC | CAG | GGG | CCT | TCA | CTG | TTC | AGT | GTC | ACT | AAG | AAG | CAG | 48 |
| CTG | GGG | GCA | GGA | AGC | AGA | GAA | GAA | TGT | GCA | GCA | AAA | TGT | GAA | GAG | GAC | 96 |
| AAA | GAA | TTC | ACC | TGC | AG | | | | | | | | | | | 113 |

| | | | | | |
|---|---|---|---|---|---|
| GTATTTTCAT | CGTCGTTGCA | CCTACCCAGA | AATCTGTAAT | TCAGATTATT | AATAAACATT | 173 |
| TGTTTTCTTT | AAATAAAGAA | AAATACTTAT | TGGATTTCCT | GCTTCGTTCT | GCAG | 227 |

| | | | | | | | | | | | |
|---|---|---|---|---|---|---|---|---|---|---|---|
| G | GCA | TTC | CAA | TAT | CAC | AGT | AAA | GAG | CAA | CAG | TGT | GTG | ATA | ATG | GCT | 273 |
| GAA | AAC | A | | | | | | | | | | | | | | 280 |

(2) INFORMATION FOR SEQ ID NO: 4

(i) SEQUENCE CHARACTERISTICS:
      (A) LENGTH: 55
      (B) TYPE: amino acid
      (D) TOPOLOGY: linear (xi) SEQUENCE DESCRIPTION: SEQ ID NO: 4:

| Tyr | Val | Asn | Thr | Gln | Gly | Pro | Ser | Leu | Phe | Ser | Val | Thr | Lys | Lys | Gln |
|---|---|---|---|---|---|---|---|---|---|---|---|---|---|---|---|
| 1 | | | | 5 | | | | | 10 | | | | | 15 | |
| Leu | Gly | Ala | Gly | Ser | Arg | Glu | Glu | Cys | Ala | Ala | Lys | Cys | Glu | Glu | Asp |
| | | | 20 | | | | | 25 | | | | | 30 | | |
| Lys | Glu | Phe | Thr | Cys | Arg | Ala | Phe | Gln | Tyr | His | Ser | Lys | Glu | Gln | Gln |
| | | | 35 | | | | | 40 | | | | | 45 | | |
| Cys | Val | Ile | Met | Ala | Glu | Asn | | | | | | | | | |
| | | | 50 | | | 55 | | | | | | | | | |

(2) INFORMATION FOR SEQ ID NO: 5

(i) SEQUENCE CHARACTERISTICS:
      (A) LENGTH: 24
      (B) TYPE: nucleic acid
      (C) STRANDEDNESS: single
      (D) TOPOLOGY: linear (xi) SEQUENCE DESCRIPTION: SEQ ID NO: 5:

GGTCAAGGAG AGCCTCTGGA TGAC                                                                 24

(2) INFORMATION FOR SEQ ID NO: 6:

(i) SEQUENCE CHARACTERISTICS:
      (A) LENGTH: 23
      (B) TYPE: nucleic acid
      (C) STRANDEDNESS: single
      (D) TOPOLOGY: linear (xi) SEQUENCE DESCRIPTION: SEQ ID NO: 6:

CCTAATGATT ATGGAGGACT TCC                                                                  23

(2) INFORMATION FOR SEQ ID NO: 7:

(i) SEQUENCE CHARACTERISTICS:
      (A) LENGTH: 24
      (B) TYPE: nucleic acid (C) STRANDEDNESS: single
        (D) TOPOLOGY: linear (xi) SEQUENCE DESCRIPTION: SEQ ID NO: 7:

CTTCGGTTCC CATGGCAGTT GGTG                                                              24

(2) INFORMATION FOR SEQ ID NO: 8:

(i) SEQUENCE CHARACTERISTICS:
        (A) LENGTH: 29
        (B) TYPE: nucleic acid
        (C) STRANDEDNESS: single
        (D) TOPOLOGY: linear (xi) SEQUENCE DESCRIPTION: SEQ ID NO: 8:

GGAAGAACCA AATGTGGCCC TGGGCATCC                                                         29

(2) INFORMATION FOR SEQ ID NO: 9:

(i) SEQUENCE CHARACTERISTICS:
        (A) LENGTH: 23
        (B) TYPE: nucleic acid
        (C) STRANDEDNESS: single
        (D) TOPOLOGY: linear (xi) SEQUENCE DESCRIPTION: SEQ ID NO: 9:

TAACGAACGA GACTCTGGCA TGC                                                               23

(2) INFORMATION FOR SEQ ID NO: 10:

(i) SEQUENCE CHARACTERISTICS:
        (A) LENGTH: 23
        (B) TYPE: nucleic acid
        (C) STRANDEDNESS: single
        (D) TOPOLOGY: linear (xi) SEQUENCE DESCRIPTION: SEQ ID NO: 10:

AGCTTATGAC CCGCACTTAC TGG                                                               23

(2) INFORMATION FOR SEQ ID NO:11:

(i) SEQUENCE CHARACTERISTICS:
        (A) LENGTH: 315 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

ATGGAACATA AGGAAGTGGT TCTTCTACTT CTTTTATTTC TGAAATCAGG TCAAGGAGAG         60

CCTCTGGATG ACGTCAAGGA GAGCCCCTGG ATGACTATGT GAATACCCAG GGGCCTTCAC        120

TGTTCAGTGT CACTAAGAAG CAGCTGGGGG CAGGAAGCAG AGAAGAATGT GCAGCAAAAT        180

GTGAAGAGGA CAAAGAATTC ACCTGCAGGG CATTCCAATA TCACAGTAAA GAGCAACAGT        240

GTGTGATAAT GGCTGAAAAC AGGAAGTCCT CCATAATCAT TAGGATGAGA GATGCAGTTT        300

TATTTGAAAA GTAAA                                                        315

I claim:

1. Substantially pure plasmilar polypeptide, said polypeptide comprising the amino acid sequence shown in FIG. 1 (SEQ ID NO:4).

* * * * *

UNITED STATES PATENT AND TRADEMARK OFFICE
CERTIFICATE OF CORRECTION

Page 1 of 2

PATENT NO. : 5,545,717

DATED : August 13, 1996

INVENTOR(S) : Lawrence Weissbach

It is certified that error appears in the above-identified patent and that said Letters Patent is hereby corrected as shown below:

In the Sequence Listing, replace the information for SEQ ID NO:11 with the following:

--(2) INFORMATION FOR SEQ ID NO:11:

(i) SEQUENCE CHARACTERISTICS:
        (A) LENGTH: 291 base pairs
        (B) TYPE: nucleic acid
        (C) STRANDEDNESS: single
        (D) TOPOLOGY: linear     (ii) MOLECULE TYPE: DNA     (xi) SEQUENCE DESCRIPTION: SEQ ID NO:11:

```
ATGGAACATA AGGAAGTGGT TCTTCTACTT CTTTTATTTC TGAAATCAGG TCAAGGAGAG     60

CCCCTGGATG ACTATGTGAA TACCCAGGGG CCTTCACTGT TCAGTGTCAC TAAGAAGCAG    120

CTGGGGGCAG GAAGCAGAGA AGAATGTGCA GCAAAATGTG AAGAGGACAA AGAATTCACC    180

TGCAGGGCAT TCCAATATCA CAGTAAAGAG CAACAGTGTG TGATAATGGC TGAAAACAGG    240
```

UNITED STATES PATENT AND TRADEMARK OFFICE
CERTIFICATE OF CORRECTION

PATENT NO. : 5,545,717
DATED : August 13, 1996
INVENTOR(S) : Lawrence Weissbach

It is certified that error appears in the above-identified patent and that said Letters Patent is hereby corrected as shown below:

AAGTCCTCCA TAATCATTAG GATGAGAGAT GCAGTTTTAT TTGAAAAGTA A         291 —

Signed and Sealed this

Tenth Day of August, 1999

Attest:

Q. TODD DICKINSON

*Attesting Officer*     Acting Commissioner of Patents and Trademarks